US009675675B2

(12) United States Patent
Zhang et al.

(10) Patent No.: US 9,675,675 B2
(45) Date of Patent: Jun. 13, 2017

(54) MICRONEEDLE DEVICE HAVING A PEPTIDE THERAPEUTIC AGENT AND AN AMINO ACID, METHODS OF MAKING AND USING THE SAME

(71) Applicant: 3M INNOVATIVE PROPERTIES COMPANY, St. Paul, MN (US)

(72) Inventors: Ying Zhang, Woodbuy, MN (US); Percy T. Fenn, St. Paul, MN (US); Peter R. Johnson, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/361,802

(22) PCT Filed: Nov. 30, 2012

(86) PCT No.: PCT/US2012/067278
§ 371 (c)(1),
(2) Date: May 30, 2014

(87) PCT Pub. No.: WO2013/082418
PCT Pub. Date: Jun. 6, 2013

(65) Prior Publication Data
US 2014/0330198 A1 Nov. 6, 2014

Related U.S. Application Data

(60) Provisional application No. 61/565,247, filed on Nov. 30, 2011, provisional application No. 61/565,227, filed on Nov. 30, 2011.

(51) Int. Cl.
| | | |
|---|---|---|
| A61K 38/00 | (2006.01) | |
| A61M 5/24 | (2006.01) | |
| A61K 38/29 | (2006.01) | |
| A61K 9/00 | (2006.01) | |
| A61M 37/00 | (2006.01) | |
| A61K 31/4172 | (2006.01) | |
| A61K 47/18 | (2017.01) | |
| A61K 38/23 | (2006.01) | |
| A61K 38/28 | (2006.01) | |
| A61K 38/47 | (2006.01) | |
| A61K 31/198 | (2006.01) | |
| A61L 31/10 | (2006.01) | |
| A61L 31/16 | (2006.01) | |
| A61K 38/22 | (2006.01) | |
| A61K 47/22 | (2006.01) | |

(52) U.S. Cl.
CPC ............ *A61K 38/29* (2013.01); *A61K 9/0021* (2013.01); *A61K 9/0087* (2013.01); *A61K 31/198* (2013.01); *A61K 31/4172* (2013.01); *A61K 38/225* (2013.01); *A61K 38/23* (2013.01); *A61K 38/28* (2013.01); *A61K 38/47* (2013.01); *A61K 47/183* (2013.01); *A61K 47/22* (2013.01); *A61L 31/10* (2013.01); *A61L 31/16* (2013.01); *A61M 37/0015* (2013.01); *A61L 2300/214* (2013.01); *A61L 2300/252* (2013.01); *A61M 2037/0023* (2013.01); *A61M 2037/0046* (2013.01); *A61M 2037/0053* (2013.01)

(58) Field of Classification Search
None
See application file for complete search history.

(56) References Cited

U.S. PATENT DOCUMENTS

| | | |
|---|---|---|
| 5,691,312 A | 11/1997 | Paques |
| 6,120,761 A | 9/2000 | Yamazaki |
| 6,881,203 B2 | 4/2005 | Delmore |
| 7,056,886 B2 | 6/2006 | Isaacs |
| 7,141,544 B2 | 11/2006 | Somers |
| 7,186,683 B2 | 3/2007 | Henriksen |
| 7,335,377 B2 | 2/2008 | Stern |
| 7,558,625 B2 | 7/2009 | Levin |
| 7,803,770 B2 | 9/2010 | Dey |
| 2002/0107505 A1 | 8/2002 | Holladay |
| 2002/0177839 A1 | 11/2002 | Cormier |
| 2004/0265354 A1 | 12/2004 | Ameri et al. |
| 2004/0265365 A1* | 12/2004 | Daddona ............... A61B 17/205 424/449 |
| 2005/0106209 A1 | 5/2005 | Ameri |
| 2005/0261631 A1 | 11/2005 | Clarke |
| 2005/0276823 A1 | 12/2005 | Cini |

(Continued)

FOREIGN PATENT DOCUMENTS

| | | |
|---|---|---|
| KR | 10-2006-0126063 | 7/2006 |
| KR | 10-2008-0110681 | 10/2008 |
| WO | WO 2004-007520 | 1/2004 |
| WO | WO 2005-051455 | 6/2005 |
| WO | WO 2005-113008 | 12/2005 |
| WO | WO 2006-079019 | 7/2006 |
| WO | WO 2006079019 A2 * | 7/2006 |
| WO | WO 2008-063279 | 5/2008 |
| WO | WO 2008-157425 | 12/2008 |
| WO | WO 2009/053106 | 4/2009 |

(Continued)

OTHER PUBLICATIONS

International Search Report for PCT International Application No. PCT/US2012/067278, mailed on Mar. 11, 2013, 3pgs.

(Continued)

*Primary Examiner* — Jeanette Lieb

(57) ABSTRACT

A medical device including an array of microneedles and a coating disposed on or within the microneedles and a method of making such a device are disclosed. The coating includes a peptide therapeutic agent and an amino acid. A method of stabilizing a peptide therapeutic agent with an amino acid on an array of microneedles is also disclosed. In some cases, the peptide therapeutic agent and the amino acid either both have a net positive charge or both have a net negative charge. In some cases, the peptide therapeutic agent is histidine.

20 Claims, 2 Drawing Sheets

(56) References Cited

U.S. PATENT DOCUMENTS

| | | |
|---|---|---|
| 2006/0115472 A1 | 6/2006 | Li |
| 2006/0188555 A1* | 8/2006 | Cormier .............. A61K 9/0021 424/448 |
| 2007/0184096 A1 | 8/2007 | Ameri |
| 2007/0249520 A1 | 10/2007 | Gore |
| 2007/0287949 A1 | 12/2007 | Levin |
| 2008/0039775 A1 | 2/2008 | Ameri et al. |
| 2008/0051699 A1 | 2/2008 | Choi |
| 2008/0269685 A1 | 10/2008 | Singh |
| 2009/0069226 A1 | 3/2009 | Ong |
| 2009/0117158 A1 | 5/2009 | Ameri et al. |
| 2009/0305965 A1 | 12/2009 | Kang |
| 2010/0092566 A1 | 4/2010 | Alessi |
| 2010/0151247 A1 | 6/2010 | Moore |
| 2010/0203014 A1 | 8/2010 | Maggio |
| 2011/0046052 A1 | 2/2011 | Yang |
| 2011/0276028 A1 | 11/2011 | Singh |
| 2011/0288485 A1 | 11/2011 | Tokumoto |
| 2012/0150023 A1 | 6/2012 | Kaspar et al. |
| 2013/0006217 A1 | 1/2013 | Hattersley et al. |
| 2013/0123707 A1 | 5/2013 | Determan et al. |
| 2014/0046292 A1 | 2/2014 | Hattersley et al. |
| 2014/0046293 A1 | 2/2014 | Hattersley et al. |
| 2014/0343499 A1 | 11/2014 | Zhang |

FOREIGN PATENT DOCUMENTS

| | | |
|---|---|---|
| WO | WO 2009/137093 | 11/2009 |
| WO | WO 2010/022176 | 2/2010 |
| WO | WO 2010-059605 | 5/2010 |
| WO | WO 2010-124255 | 10/2010 |
| WO | WO 2011-014514 | 2/2011 |
| WO | WO 2011-051916 | 5/2011 |
| WO | WO 2011-085393 | 7/2011 |
| WO | WO 2011-150144 | 12/2011 |
| WO | WO 2012-145665 | 10/2012 |

OTHER PUBLICATIONS

Zhang, "Inhibition of Peptide Acylation in PLGA Microspheres with Water-soluble Divalent Cationic Salts", Pharmaceutical Research, 2009, vol. 26, No. 8, pp. 1986-1994.

* cited by examiner

US 9,675,675 B2

MICRONEEDLE DEVICE HAVING A PEPTIDE THERAPEUTIC AGENT AND AN AMINO ACID, METHODS OF MAKING AND USING THE SAME

CROSS-REFERENCE TO RELATED APPLICATION

This application is a national stage filing under 35 U.S.C. 371 of PCT/US2012/067278, filed Nov. 30, 2012, which claims priority to U.S. Application Nos. 61/565,227 and 61/565,247, both filed Nov. 30, 2011, the disclosures of which are incorporated by reference in their entirety herein.

BACKGROUND

Transdermal delivery of a therapeutic agent such as a drug through the skin to the local tissue or systemic circulatory system without piercing the skin, such as with a transdermal patch, has been used successfully with a limited number of therapeutic molecules. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below.

Microneedle devices having a fluid reservoir and conduits through which a therapeutic substance may be delivered to the skin have been proposed, but there remain a number of difficulties with such systems, such as expense and the ability to make very fine channels that can reliably be used for fluid flow.

Microneedle devices having a dried coating on the surface of a microneedle array have also been developed. The devices are generally simpler than microneedle devices having fluid reservoirs and may directly introduce a therapeutic substance into the skin without the need for providing reliable control of fluid flow through very fine channels in the microneedle device.

SUMMARY

A challenging task in the development of peptide therapeutic agents, particularly polypeptides and proteins, is addressing physical (e.g., adsorption, aggregation, denaturation, or precipitation) and chemical (e.g, hydrolysis, oxidation, acylation, or deamidation) instability, which may cause loss of biological activity. It has now been found that the addition of an amino acid typically enhances the stability of a peptide therapeutic agent coated on a transdermal delivery device having an array of skin-piercing microneedles.

In one aspect, the present disclosure provides a medical device including an array of microneedles a coating on or within at least a portion of the microneedles. The coating includes a peptide therapeutic agent and an amino acid, wherein the peptide therapeutic agent and the amino acid either both have a net positive charge or both have a net negative charge. The coating can be substantially free of sorbitol.

In another aspect, a method of making such a medical device is disclosed. The method typically includes:

providing an aqueous composition comprising a peptide therapeutic agent, an amino acid, and a buffer, wherein the peptide therapeutic agent and the amino acid either both have a net positive charge or both have a net negative charge in the aqueous composition;

contacting the microneedles with the composition; and volatilizing a portion of the aqueous composition to provide a coating on a least a portion of the microneedles, wherein the coating comprises at least the peptide therapeutic agent and the amino acid.

In another aspect, the present disclosure provides a medical device including an array of microneedles a coating on or within at least a portion of the microneedles. The coating includes a peptide therapeutic agent and histidine. The molar ratio of the histidine to the peptide therapeutic agent can be less than 2:1.

In another aspect, a method of making such a medical device is disclosed. The method typically includes:

providing an aqueous composition comprising a peptide therapeutic agent, histidine, and a buffer, wherein the molar ratio of the histidine to the peptide therapeutic agent is less than 2:1;

contacting the microneedles with the composition; and volatilizing a portion of the aqueous composition to provide a coating on a least a portion of the microneedles, wherein the coating comprises at least the peptide therapeutic agent and the histidine.

In another aspect, the present disclosure provides a method of stabilizing a peptide therapeutic agent on or within an array of microneedles, the method comprising incorporating an amino acid into the array of microneedles. In some embodiments, the peptide therapeutic agent and the amino acid either both have a net positive charge or both have a net negative charge. In some embodiments, the amino acid is histidine. In some embodiments, the molar ratio of the amino acid (e.g., histidine) to the peptide therapeutic agent is less than 2:1.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

As used in this specification and the appended claims, the term "or" is generally employed in its sense including "and/or" unless the content clearly dictates otherwise. For example, "a coating on or within at least a portion of the microneedles" means the coating is on and/or within at least a portion of the microneedles.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The term "peptide" as used herein refers to peptides, polypeptides, and proteins. The terms "peptide", "polypeptide", and "protein" are interchangeable in the context of the present disclosure. These terms refer to a molecule having at least two amino acids linked through peptide bonds. The terms include oligopeptides, protein fragments, analogs, derivatives (e.g., glycosylated derivatives and pegylated derivatives), and fusion proteins.

All scientific and technical terms used herein have meanings commonly used in the art unless otherwise specified. The definitions provided herein are to facilitate understanding of certain terms used frequently herein and are not meant to limit the scope of the present disclosure.

In embodiments where weight percent is based upon total weight of solids, solids are those ingredients which are not volatile. For example, the total weight of solids does not include a volatilizable carrier (e.g., water or a volatile co-solvent).

The above summary of the present invention is not intended to describe each disclosed embodiment or every implementation of the present invention. The description that follows more particularly exemplifies illustrative embodiments. In the application, guidance is provided through lists of examples, which examples can be used in various combinations. In each instance, the recited list serves only as a representative group and should not be interpreted as an exclusive list.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION OF ILLUSTRATIVE EMBODIMENTS

Figure 1:
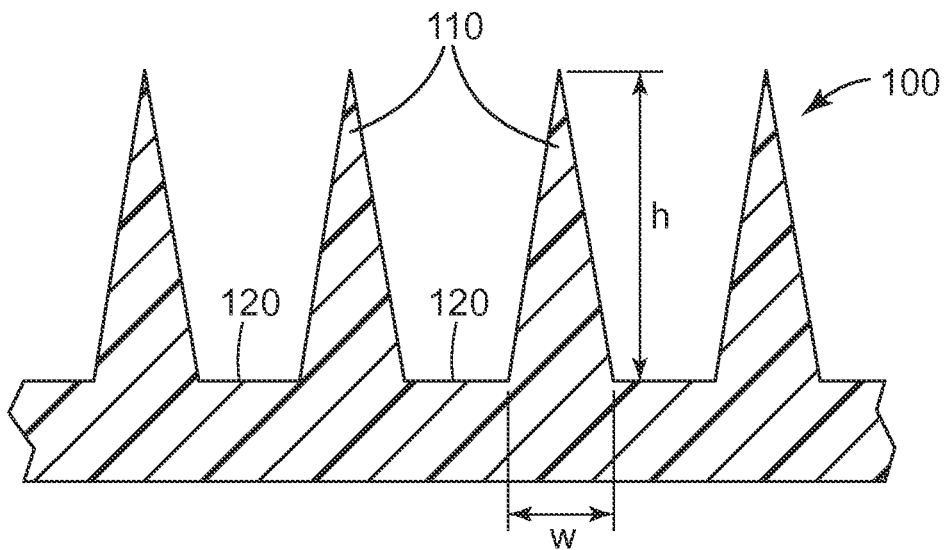
FIG. 1 is a schematic cross-sectional view of an uncoated microneedle array.

In the following description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

With the development of recombinant DNA technology, a number of peptide therapeutic agents have become available for therapeutic use. These agents include octreotide, leuprolide, parathyroid hormone, luteinizing hormone releasing hormone, insulin, vascular endothelial growth factor, and many others. One challenging task in the development of peptide therapeutic agents is addressing physical (e.g., adsorption, aggregation, denaturation, or precipitation) and chemical (e.g., hydrolysis, oxidation, acylation, or deamidation) instability, which may cause loss of biological activity.

Oxidation is a major chemical degradation pathway of peptide therapeutic agents. The side chains of His, Met, Cys, Trp and Tyr residues in proteins are potential sites for oxidation. Some proteins are very sensitive to light during manufacturing and storage, which can also result in modification of the molecules. Both oxygen content and light exposure may cause oxidation and affect oxidation rate and promote aggregation or other degradation pathways. Oxidation can alter a protein's physiochemical characteristics and led to aggregation or fragmentation, which can negatively impact potency and immunogenicity. Acylation is another pathway of instability of peptide therapeutic agents. Nucleophilic primary amines, such as at the N-terminus or a lysine side chain, can react with carboxylate groups to form acylated peptide adducts. Peptide acylation may cause loss of activity, a change of receptor specificity, or immunogenicity. Protein aggregation is an example of physical instability, and aggregate formation can lead to loss of biological activity, loss of solubility, and increased immunogenicity.

These and other degradation pathways can result in loss of activity. It is therefore desirable to provide compositions for formulating and delivering peptide therapeutic agents having enhanced chemical and physical stability and exhibiting maximal shelf lives. It has now been found that amino acids are useful for stabilizing peptide therapeutic agents coated on and/or within a medical device having a plurality of skin-piercing microneedles. Without wishing to be bound by theory, it is believed that the addition of the amino acid substantially reduces the oxidation, photo-oxidation, acylation, and aggregation of peptide formulations.

A number of peptide therapeutic agents may usefully be incorporated into the medical devices according to and/or made according to the present disclosure. Exemplary peptide therapeutic agents include parathryoid hormone, calcitonin, lysozyme, insulin, glatiramer acetate, goserelin acetate, somatostatin, octreotide, leuprolide, vasopressin, thymosin alpha-1, atrial natriuretic peptide (ANP), endorphin, growth factors (e.g., vascular endothelial growth factor (VEGF), fibroblast growth factor (FGF), erythropoietin (EPO), bone morphogenetic proteins (BMPs), and epidermal growth factor (EFG), granulocyte colony-stimulating factor (G-CSF), granulocyte macrophage colony stimulating factor (GM-CSF), insulin-like growth factor (IGF), platelet-derived growth factor releasing factor), growth hormone release hormone (GHRH), interferons (e.g., interferon alpha, interferon beta, and interferon gamma), antimicrobial peptides, dornase alfa, tissue plasminogen activator, urokinase, ANP clearance inhibitors, luteinizing hormone releasing hormone (LHRH), Melanocyte Stimulating Hormones (alpha & Beta MSH), pituitary hormones (hGH), Adrenocorticotropic hormone (ACTH), human chorionic gonadotropin, streptokinase, interleukins, menotropins (urofollitropin (FSH) and LH)), protein C, protein S, angiotensin, angiogenin, Endothelins, pentigetide, Brain natriuretic peptide (BNP), neuropeptide Y, Islet Amyloid Polypeptide (IAPP), Vasoactive intestinal peptide (VIP), hirudin, glucagon, insulin, insulinotropin analogs and derivatives of any of the foregoing peptide therapeutic agents, fusion proteins, and peptide vaccines. Peptide vaccines include those with an antigen in the form of a peptide as defined above. Exemplary peptide vaccines include therapeutic cancer vaccine, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, polio vaccine, herpes vaccine, human papilloma virus vaccine, rotavirus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. In some embodiments, the peptide vaccine includes at least one of influenza vaccine, polio vaccine, hepatitis A vaccine, and cancer vaccine.

A number of amino acids may usefully be incorporated into the medical devices according to and/or made according to the present disclosure. Useful amino acids include naturally occurring amino acids and synthetic amino acids that are capable of having a net positive charge or a net negative charge. Typically, useful amino acids are capable of having a net positive charge or a net negative charge in a pH range from 3 to 11. The amino acids may have either L- or D-Fischer configuration. In some embodiments, the amino acid is histidine, arginine, lysine, aspartic acid, or glutamic acid. In some embodiments, the amino acid is histidine, lysine, or arginine. Such amino acids can be useful, in some embodiments, with peptide therapeutic agents having a net positive charge. In some embodiments, the amino acid is aspartic acid or glutamic acid. Such amino acids can be useful, in some embodiments, with peptide therapeutic agents having a net negative charge. In some embodiments, the amino acid is histidine. In the coatings disclosed herein or in a coating formulation, which may be an aqueous composition, the amino acid may be in salt form.

In many embodiments, the peptide therapeutic agent and the amino acid either both have a net positive charge or both have a net negative charge. In some embodiments, the peptide therapeutic agent and the amino acid each have a net positive charge. For example, the peptide therapeutic agent may be parathyroid hormone, lysozyme, insulin, or salmon calcitonin, and the amino acid may be histidine, arginine, or lysine. In other embodiments, the peptide therapeutic agent and the amino acid each have a net negative charge. For example, the peptide therapeutic agent may be insulin, and the amino acid may be aspartic acid or glutamic acid. In embodiments where the peptide therapeutic agent and the amino acid each have a net positive charge and in embodiments where the peptide therapeutic agent and the amino acid each have a net negative charge, it may be said that the peptide therapeutic agent and the amino acid have the same charge or matched charges. That is, the charge on the peptide therapeutic agent and the amino acid might be considered the same or matched if the charge is in the same direction, regardless of the magnitude of the charge. An amino acid that has a net negative charge or a net positive charge may not be said to be a zwitterion (that is, neutral).

The net charges of the peptide therapeutic agent and the amino acid are typically established in a formulation that is used to coat the array of microneedles in the methods described hereinbelow. Typically, the peptide therapeutic agent and the amino acid are dissolved or dispersed in a solvent at an established pH. For example, the pH may be in a range from 3 to 11, 4 to 10, 6 to 8, or 5.5 to 8.5. In some embodiments wherein the amino acid is histidine, the pH may be in a range from 3 to 6, 3 to 5, 3 to 4, or 4 to 5. The formulation can be an aqueous composition that is buffered at a particular formulation pH. When a portion of the aqueous composition is volatized after coating the array of microneedles with the composition, the peptide therapeutic agent and the amino acid maintain their net charges and are incorporated into the coating.

Amino acids having a net charge may be said to be substantially in charged form since there is usually equilibrium between charged and neutral species. In some embodiments, the ratio of the charged form of the amino acid to the neutral form that may be present can be at least 10:1. In some embodiments, the ratio of the charged form of the amino acid to the neutral form is at least 100:1, at least 1000:1, or at least 10,000:1. Such ratios can be determined in solution, for example, using the difference between the formulation pH and the pKa of the amino acid side chain. Amino acids useful for practicing the present disclosure are considered to have a net positive charge if their isoelectric points are higher than the formulation pH. Amino acids useful for practicing the present disclosure are considered to have a net negative charge if their isoelectric points are lower than the formulation pH.

For peptide therapeutic agents, when the isoelectric point is lower than the pH of the formulation, it typically is described as having a net negative charge. When the isoelectric point of the peptide therapeutic agent is higher than the pH of the formulation, it typically is described as having a net positive charge.

In some embodiments, it may be useful to define the net charges of the amino acid and the peptide therapeutic agent at physiological pH (e.g., in a range from 7 to 7.4). In these embodiments, if an isoelectric point of a peptide therapeutic agent is less than about 7, it typically is described as having a net negative charge. If an isoelectric point of a peptide therapeutic agent is greater than about 7, it typically is described as having a net positive charge.

In contrast to U.S. Pat. App. Pub. No. 2006/0188555 (Cormier et al.), which suggests that therapeutic peptide agents should be formulated with particular counterions to limit fibril formation in a formulation, it has now been found that formulations and coatings including peptide therapeutic agent and amino acids that do not have opposite net charges have useful physical and chemical stability. In embodiments where the peptide therapeutic agent and the amino acid either both have a net positive charge or both have a net negative charge, the amino acids cannot be considered to be counterions for the peptide therapeutic agents.

In some embodiments, the amino acid is histidine. Histidine may be useful in coatings containing a peptide therapeutic agent with either a net positive charge or a net negative charge. In coatings disclosed herein, histidine may stabilize a wide variety of peptide therapeutic agents (e.g., both net negatively charged and net positively charged) to at 40° C. and 96% relative humidity to a greater extent that several other amino acids.

In the medical device according to and/or made according to the present disclosure, the amino acid may be present in a variety of useful amounts relative to the peptide therapeutic agent. In some embodiments, including any one of the above embodiments, the molar ratio of the amino acid to the peptide therapeutic agent is in a range from 0.25:1 to 51:1. In some embodiments, the molar ratio of the amino acid to the peptide therapeutic agent is in a range from 0.5:1 to 25:1 or 0.5:1 to 20:1. Advantageously, in many embodiments, a large excess of the amino acid is not required. In these embodiments, the molar ratio of the amino acid to the peptide therapeutic agent may be less than 2:1, less than 1.5:1, or less than 1:1. For example, the molar ratio of the amino acid to the peptide therapeutic agent may be in a range from 0.5:1 to 2:1, 0.5:1 to 1.5:1, or 0.5:1 to 1:1. In embodiments where molar ratio of the amino acid to the peptide therapeutic agent may be less than 2:1, less than 1.5:1, or less than 1:1, the amino acids would generally not be considered to be present in a sufficient amount to neutralize the peptide therapeutic agents.

In some embodiments, including any one of the above embodiments, particularly when the coating is on an external surface of the microneedles or on an interior surface of hollow microneedles, the amino acid is present in an amount of at least 0.1 weight percent based upon total weight of solids in the coating, in some embodiments at least 0.5 weight percent, in some embodiments at least 1 weight percent, and in some embodiments at least 2 weight percent. In some embodiments, the amino acid is present in an amount of up to 25 weight percent, in some embodiments, up to 15 weight percent, in some embodiments up to 10, 9, or 8 weight percent, based upon the total weight of solids in the coating. In some embodiments, the amino acid is present in an amount of 0.1 weight percent to 20 weight percent, 0.1 weight percent to 10 weight percent, or 1 weight percent to 8 weight percent, based upon total weight of solids in the coating.

In some embodiments, including any one of the above embodiments, particularly when the coating is on an external surface of the microneedles or on an interior surface of hollow microneedles, the peptide therapeutic agent is present in an amount of at least 10 weight percent based upon total weight of solids in the coating, in some embodiments at least 20 weight percent, in some embodiments at least 50 weight percent, and in some embodiments at least 60 weight percent. In some embodiments, the peptide therapeutic agent is present in an amount of up to 99.9 weight percent, in some embodiments, up to 99.5 weight percent, in some embodiments up to 99, 95, or 92 weight percent, based on the total weight of solids in the coating. In some embodiments, the peptide therapeutic agent is present in an amount of 10 weight percent to 99.9 weight percent, 50 weight percent to 99.5 weight percent, or 50 weight percent to 95 weight percent, based upon total weight of solids in the coating.

The coatings disclosed herein may also contain at least one excipient. An excipient can function to maintain the active nature of the peptide therapeutic agent, to facilitate the performance of a coating formulation when depositing a coating on the microneedles, to resist disruption of the coating or the microneedle structure itself when penetrating the stratum corneum or other tissue, or a combination thereof. Exemplary excipients include, for example, buffers, carbohydrates, polymers, surfactants, non-volatile non-aqueous solvents, acids, bases, antioxidants, saccharin (e.g., saccharin sodium dehydrate), lipids (e.g., dipalmitoylphosphatidylcholine (DPPC)), and inorganic salts (e.g., sodium chloride and potassium chloride).

The amount of the at least one excipient in the coating and therefore in the coating formulation used for depositing the coating can vary depending on at least one of the identity of the components in the coating formulation, the amount of peptide therapeutic agent and amino acid desired on the microneedle array, the type of microneedle array being coated, the shape and location of the coating on the microneedle, or other considerations.

In some embodiments, the method of making a medical device including microneedles according to the present disclosure includes providing an aqueous composition comprising a peptide therapeutic agent, an amino acid, and a buffer. Similarly, aqueous compositions disclosed herein useful for coating an array of microneedles typically include the peptide therapeutic agent, the amino acid, and a buffer. A buffer generally functions to stabilize the pH of a coating formulation used for depositing the coating on the microneedles. The particular buffer to be utilized can depend at least in part on the particular peptide therapeutic agent and amino acid that are included in the coating. The pH of the formulation can, for example, help to maintain the solubility of the peptide therapeutic agent and amino acid in the composition. As described above, the pH also generally controls the charges on the amino acid and the peptide therapeutic agent.

A variety of buffers can be useful in the aqueous compositions useful for practicing the present disclosure. Exemplary buffers include histidine, phosphate buffers, acetate buffers, citrate buffers, glycine buffers, ammonium acetate buffers, succinate buffers, pyrophosphate buffers, Tris acetate (TA) buffers, and Tris buffers. Buffered saline solutions can also be utilized as buffers. Exemplary buffered saline solutions include phosphate buffered saline (PBS), Tris buffered saline (TBS), saline-sodium acetate buffer (SSA), and saline-sodium citrate buffer (SSC). In some embodiments, phosphate buffered saline is used for the aqueous composition. A wide variety of pH values may be useful depending, for example, on the peptide therapeutic agent and the amino acid. In some embodiments, the pH may be in a range from 3 to 11, 4 to 10, 6 to 8, or 5.5 to 8.5. In some embodiments, for example, wherein the amino acid is histidine, the pH may be in a range from 3 to 6, 3 to 5, or 4 to 5.

It should be understood that in aqueous compositions disclosed herein that include a peptide therapeutic agent, an amino acid, and a buffer, a single amino acid cannot serve as both the amino acid component and the buffer. For example, in aqueous compositions including a peptide therapeutic agent, an amino acid, and a buffer in which histidine is used as a buffer, another amino acid is present as the amino acid component. Furthermore, it should be understood that the amino acid in the aqueous compositions useful for practicing the present disclosure does not necessarily buffer the aqueous composition.

In some embodiments, the coating comprising the peptide therapeutic agent and the amino acid or the aqueous composition disclosed herein further comprises a carbohydrate. The carbohydrate may be useful, for example, for stabilizing the aqueous composition containing a peptide therapeutic agent useful for coating the microneedles in the method disclosed herein. The carbohydrate can be a saccharide, including mono-, di-, and polysaccharides, and may include, for example, non-reducing sugars such as raffinose, stachyose, sucrose, and trehalose; and reducing sugars such as monosaccharides and disaccharides. Exemplary monosaccharides include apiose, arabinose, digitoxose, fucose, fructose, galactose, glucose, gulose, hamamelose, idose, lyxose, mannose, ribose, tagatose, sorbitol, xylitol, and xylose. Exemplary disaccharides include sucrose, trehalose, cellobiose, gentiobiose, lactose, lactulose, maltose, melibiose, primeverose, rutinose, scillabiose, sophorose, turanose, and vicianose. In embodiments, sucrose, trehalose, fructose, maltose, or combinations thereof can be utilized. All optical isomers of exemplified sugars (D, L, and racemic mixtures) are also included herein. Useful polysaccharides include starches such as hydroxyethyl starch, pregelatinized corn starch, pentastarch, dextrin, dextran or dextran sulfate, gamma-cyclodextrin, alpha-clyclodextrin, beta-clyclodextrin, glucosyl-alpha-cylcodextrin, maltosyl-alpha-cyclodextrin, glucosyl-beta-cyclodextrin, maltosyl-beta-cyclodextrin, 2-hydroxy-beta-cyclodextrin, 2-hydroxypropyl-beta-cyclodextrin, 2-hydroxypropyl-gamma-cyclodextrin, hydroxyethyl-beta-cyclodextrin, methyl-beta-cyclodextrin, sulfobutylether-alpha-cyclodextrin, sulfobutylether-beta-cyclodextrin, and sulfobutylether-gamma-cyclodextrin. In embodiments, hydroxyethyl starch, dextrin, dextran, gamma-clyclodextrin, beta-cyclodextrin, or combinations thereof can be utilized. In embodiments, dextrans having an average molecular mass of 35,000 to 76,000 can be utilized.

In some embodiments, the at least one carbohydrate is a cellulose. Suitable celluloses include hydroxyethyl cellulose (HEC), methyl cellulose (MC), microcrystalline cellulose, hydroxypropyl methyl cellulose (HPMC), hydroxyethylmethyl cellulose (HEMC), hydroxypropyl cellulose (HPC), and mixtures thereof.

Advantageously, typically, the aqueous composition and the coating comprising the peptide therapeutic agent and the amino acid are stable even in the absence of a carbohydrate. In some of these embodiments, the aqueous composition and the coating are substantially free of a carbohydrate. For example, the aqueous composition and the coating can be substantially free of a saccharides, including mono-, di-, and polysaccharides. For example, the aqueous composition and the coating may be free of any of the mono-, di-, and polysaccharides listed above. In some embodiments of the medical device according to the present disclosure is substantially free of sorbitol. In some embodiments of the method according the present disclosure, the aqueous composition is substantially free of sorbitol. "Substantially free", referring to any carbohydrate listed above or sorbitol, means that a carbohydrate or sorbitol could be present but in an amount less than necessary to stabilize the aqueous composition or the coating. "Substantially free" of a specific carbohydrate or sorbitol includes being free of the carbohydrate or sorbitol and further includes wherein the molar amount of the carbohydrate or sorbitol is less than the molar amount of peptide therapeutic agent. In some embodiments, the term "substantially free" of a specific carbohydrate or sorbitol means that the amount of the carbohydrate or sorbitol is less than 4, 3, 2, or 1 percent by mole or by weight, based on the total amount of solids in the composition. In some embodiments, the aqueous composition and/or the coating comprising the peptide therapeutic agent and the amino acid are free of carbohydrates. In some embodiments, the aqueous composition and/or the coating comprising the peptide therapeutic agent and the amino acid are free of sorbitol.

In some embodiments, the aqueous composition and the coating disclosed herein include at least one surfactant. The at least one surfactant can be amphoteric, cationic, anionic, or nonionic. Exemplary suitable surfactants include lecithin, polysorbates (e.g., polysorbate 20, polysorbate 40, and polysorbate 80), glycerol, sodium lauroamphoacetate, sodium dodecyl sulfate, cetylpyridinium chloride (CPC), dodecyltrimethyl ammonium chloride (DoTAC), sodium desoxycholate, benzalkonium chloride, sorbitan laurate, and alkoxylated alcohols (e.g., laureth-4). Advantageously, in some embodiments, surfactants are not necessary in the coatings and the aqueous compositions disclosed herein. In some of these embodiments, the aqueous composition and the coating are substantially free of surfactant. "Substantially free of surfactant" refers to being free of surfactant or having up to 1, 0.5, 0.1, or 0.01 percent by weight surfactant, based on the total solids in the composition or coating.

Non-volatile, non-aqueous solvents may be useful in the aqueous compositions disclosed herein and may be present in the resulting coatings. Exemplary suitable non-volatile, non-aqueous solvents include propylene glycol, dimethylsulfoxide, glycerin, 1-methyl-2-pyrrolidinone, and N,N-dimethylformamide.

The aqueous compositions and the coatings disclosed herein may include at least one antioxidant. Exemplary suitable antioxidants include sodium citrate, citric acid, ascorbic acid, methionine, sodium ascorbate, and combinations thereof. Advantageously, in some embodiments, such antioxidants are not necessary in the coatings and the aqueous compositions disclosed herein. In some of these embodiments, the aqueous composition and the coating can have up to 1, 0.5, 0.1, or 0.01 percent by weight of any of these antioxidants, based on the total solids in the composition or coating.

In some embodiments, the coating or the aqueous composition disclosed herein includes at least one polymer. Exemplary useful polymers include polyvinyl pyrrolidone (PVP), polyethylene glycol (PEG), polyvinyl alcohol (PVA), and polyethylene glycol sorbitan isostearate. In some embodiments, PVPs having a number average molecular weight of 5,000 to 1.5 million may be useful. In some embodiments, polyethylene glycols having a number average molecular weight of 300 to 8,000 may be useful.

In some embodiments, the coating or the aqueous composition disclosed herein may include a polypeptide other than the peptide therapeutic agent. The amino acids making up the polypeptide may be the same or at least some may be different from each other. Exemplary useful polyamino acids (the same amino acids) can include polyhistidine, polyaspartic acid, and polylysine.

In some embodiments of the coatings and aqueous compositions, counterions for the peptide therapeutic agent and/or the amino acid are present. Exemplary weak acids useful for providing counterions for postively charged peptide therapeutic agents or amino acids include acetic acid, propionic acid, pentanoic acid, citric acid, succinic acid, glycolic acid, gluconic acid, glucuronic acid, lactic acid, malic acid, pyruvic acid, tartaric acid, tartronic acid, fumaric acid, malonic acid, butyric acid, crotonic acid, digylcolic acid, and glutaric acid. Exemplary strong acids useful for providing counterions for postively charged peptide therapeutic agents or amino acids include hydrochloric acid, hydrobromic acid, nitric acid, sulfonic acid, sulfuric acid, maleic acid, phosphoric acid, benzene sulfonic acid, and methane sulfonic acid. Exemplary weak bases useful for providing counterions for negative charged peptide therapeutic agents or amino acids include ammonia, morpholine, monoethanolamine, diethanolamine, triethanolamine, tromethamine, methylglucamine, and glucosamine. Exemplary strong bases useful for providing counterions for negative charged peptide therapeutic agents or amino acids include sodium hydroxide, potassium hydroxide, calcium hydroxide, and magnesium hydroxide.

The method of making a medical device comprising microneedles according to the present disclosure includes providing an aqueous composition comprising a peptide therapeutic agent, an amino acid, and, in some embodiments, a buffer. Accordingly, the present disclosure also provides an aqueous composition suitable for coating an array of microneedles. The aqueous composition includes a peptide therapeutic agent, an amino acid, and optionally a buffer. The amounts of these ingredients in the composition are chosen in order to achieve the above described amounts of the solid, non-volatile ingredients in the resulting coating deposited on the microneedles. The aqueous composition may further include any of the excipients described above. The coating is deposited on the microneedles by contacting the microneedles with the composition.

In addition to water, which serves as a volatilizable carrier, the aqueous composition can also include at least one co-solvent (which may also be a volatilizable carrier). Exemplary useful co-solvents, which may be volatilizable carriers, include ethanol, isopropanol, methanol, propanol, and butanol. $C_{1-4}$ ethers, $C_{1-4}$ ketones, and $C_{1-4}$ esters, for example, may also be useful. Useful volatile co-solvents are typically those having a boiling point up to 120° C., in some embodiments up to 100° C. Non-volatile co-solvents may also be included as described above. Generally, the solvent in the coating formulation is selected such that it may dissolve or disperse the peptide therapeutic agent, the amino acid, and any excipients that may be present. The aqueous compositions can have an overall solids content from 5% to 80% by weight, from 10% to 70% by weight, or from 50% to 70% by weight, based on the total weight of the aqueous composition.

Aqueous compositions useful for depositing the coating on the microneedles can be designed to have a desired viscosity, surface tension, and/or contact angle of the aqueous composition on the material comprising the microneedles.

The viscosity of the aqueous composition can be an important factor for providing a desired amount of uniform coatings on the microneedles. The desired viscosity of the aqueous composition can depend at least in part on at least one of the geometry of the microneedles, the particular coating method being utilized, and the desired number of coating steps, among other factors. In some embodiments, the aqueous composition has a shear viscosity in a range from 500 to 30,000 centipoise (cps) (in some embodiments, in a range from 500 to 10,000 cps or 500 to 8,000 cps) when measured at a shear rate of 100 s$^{-1}$ at a temperature of 25° C. The shear viscosity is a measurement of the resistance of a fluid to being deformed by shear stress. Various instruments can be used for viscosity testing, including rheometers, for example rheometers from TA Instruments (New Castle, Del.).

The surface tension of the aqueous composition can be an important factor for providing a desired amount of material on the microneedles without excessive spreading along the needle or onto the microneedle substrate. The desired surface tension of the aqueous composition can depend at least in part on at least one of the geometry of the microneedles, the particular coating method being utilized, and the desired number of coating steps, among other factors. In some embodiments, the aqueous composition has a surface tension (measured at ambient, or room temperature conditions) up to 60 dynes/cm, in some embodiments, up to 55 dynes/cm. In some embodiments, the aqueous composition has a surface tension in a range from 40 dynes/cm to 55 dynes/cm. The surface tension can be determined using the pendant drop method. In a pendant drop method of measuring surface tension, a drop of liquid is suspended from the end of a tube by surface tension. The force due to surface tension is proportional to the length of the boundary between the liquid and the tube. Various instruments that encompass optical systems for measuring the relevant parameters of the drop and software packages for calculating the surface tension based on the measured parameters can be utilized herein. An exemplary instrument includes the Drop Shape Analysis System (Model DSA 100S) available from Krüss (Hamburg, Germany).

The contact angle of the aqueous composition on the material comprising the microneedles (also referred to as the "microneedle material") can be an important factor for providing a desired amount of material on the microneedles without excessive spreading along the needle or onto the microneedle substrate. The desired contact angle of the aqueous composition on the microneedle material can depend at least in part on at least one of the composition of the microneedles, the geometry of the microneedles, the particular coating method being utilized, and the desired number of coating steps, among other factors. In some embodiments, the aqueous composition has a contact angle (measured at ambient, or room temperature conditions) with the microneedle material of at least 50 degrees, at least 55 degrees, or at least 65 degrees. The contact angle of the aqueous composition on the microneedle material can be measured using various methods, for example, using the sessile drop method. Generally, a goniometer (or an instrument that employs a goniometer) can be utilized to measure contact angles; an example of such an instrument is the Drop Shape Analysis System (Model DSA 100S) available from Krüss (Hamburg, Germany). In embodiments, the contact angle can be measured within 5 seconds of the transfer of the aqueous composition onto the substrate (microneedle material). The contact angle of the aqueous composition with respect to the microneedle material is measured on a horizontal substrate made of the microneedle material.

The microneedle material can be (or include) silicon or a metal such as stainless steel, titanium, or nickel titanium alloy. The microneedle material can also be (or include) a medical grade polymeric material. In some embodiments, including any one of the above embodiments, the microneedle material can be a medical grade polymeric material. Exemplary types of medical grade polymeric materials include polycarbonate and liquid crystalline polymer (referred to herein as "LCP").

Generally, an "array" refers to medical devices described herein that include more than one (in embodiments, a plurality) structure capable of piercing the stratum corneum to facilitate the transdermal delivery of the peptide therapeutic agent and amino acid to the skin. The terms "microstructure" and "microneedle" refer to the structures associated with an array that are capable of piercing the stratum corneum to facilitate the transdermal delivery of the peptide therapeutic agent and amino acid to the skin. By way of example, microstructures can include needle or needle-like structures as well as other structures capable of piercing the stratum corneum. The term "microneedle array" or "array of microneedles" therefore can refer to a plurality of structures that are capable of piercing the stratum corneum to facilitate the transdermal delivery of the peptide therapeutic agent and amino acid to the skin.

Microneedle arrays useful for practicing the present disclosure can have a variety of configurations, such as those described in the following patents and patent applications, the disclosures of which are incorporated herein by reference thereto. One embodiment for the microneedle arrays includes the structures disclosed in U.S. Patent Application Publication No. 2005/0261631 (Clarke et al.), which describes microneedles having a truncated tapered shape and a controlled aspect ratio. A further embodiment for the microneedle arrays includes the structures disclosed in U.S. Pat. No. 6,881,203 (Delmore et al.), which describes tapered microneedles with at least one channel formed on the outside surface. Another embodiment for the microneedle arrays includes the structures disclosed in Int. App. Pub. Nos. WO2011/014514 (Gonzalez et al.) and WO2010/059065 (Burton et al.), which both describe hollow microneedles. For hollow microneedles, either the concave surface, the convex surface, or both may include the coating disclosed herein. A coating on the concave surface may be considered "within" the microneedles. In some embodiments, the microneedles are solid microneedles (that is, the microneedles are solid throughout).

Generally, a microneedle array includes a plurality of microneedles. FIG. 1 shows a portion of a microneedle array 100 that includes four microneedles 110 (of which two are referenced in FIG. 1) positioned on a microneedle substrate 120. Each microneedle 110 has a height h, which is the length from the tip of the microneedle 110 to the microneedle base at substrate 120. Either the height of a single microneedle or the average height of all microneedles on the microneedle array can be referred to as the height of the microneedle, h. In some embodiments, including any one of the embodiments described herein, each of the plurality of microneedles (or the average of all of the plurality of microneedles) has a height of about 100 to 1200 micrometers (μm), in some embodiments about 200 to 1000 μm, or about 200 to 750 μm. In some embodiments, including any one of the embodiments described herein, the array of microneedles contains 200 to 1500 microneedles per $cm^2$ of the array of microneedles.

A single microneedle or the plurality of microneedles in a microneedle array can also be characterized by their aspect ratio. The aspect ratio of a microneedle is the ratio of the height of the microneedle, h, to the width (at the base of the microneedle), w (as seen in FIG. 1). The aspect ratio can be presented as h:w. In some embodiments, including any one of the embodiments described herein, each of the plurality of microneedles (or the average of all of the plurality of microneedles) has (have) an aspect ratio in the range of 2:1 to 5:1. In some of these embodiments, each of the plurality of microneedles (or the average of all of the plurality of microneedles) has (have) an aspect ratio of at least 3:1.

A microneedle or the plurality of microneedles in a microneedle array useful for practicing the present disclosure can have a variety of shapes. In some embodiments, including any one of the embodiments described herein, each of the plurality of microneedles can have a square pyramidal shape or the shape of a hypodermic needle. In some of these embodiments, the shape is square pyramidal.

Figure 2:
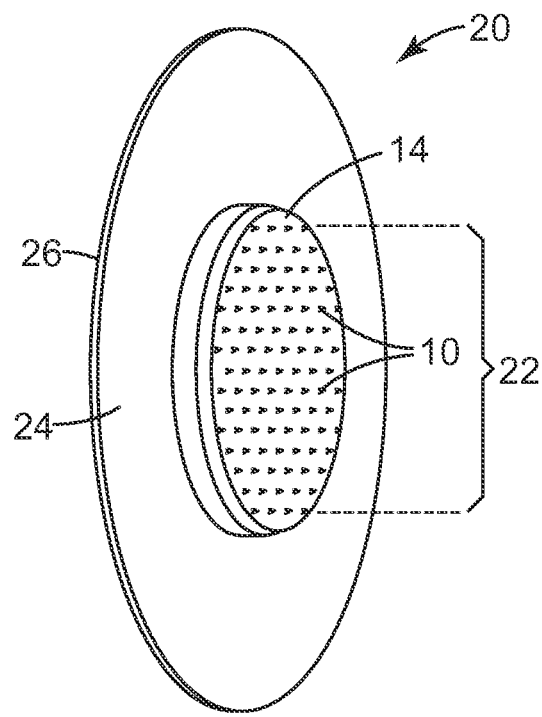
FIG. 2 is a schematic perspective view of a microneedle device in the form of a patch.

In some embodiments, including any one of the embodiments described herein, the medical device according to the present disclosure may be in the form of a patch. One example of such an embodiment is shown in more detail in FIG. 2. FIG. 2 illustrates a medical device comprising a patch 20 in the form of a combination of a microneedle array 22, pressure sensitive adhesive 24 and backing 26. Such a patch 20 or another device including multiple microneedle arrays or multiple patches 20 can be referred to as a delivery device. The microneedle array 22 is illustrated with microneedles 10 protruding from a microneedle substrate 14. The microneedles 10 may be arranged in any desired pattern or distributed over the microneedle substrate 14 randomly. As shown, the microneedles 10 are arranged in uniformly spaced rows. In some embodiments, including any one of the embodiments described herein, microneedle arrays can have a surface area on the non-structured surface of more than about 0.1 $cm^2$ and less than about 20 $cm^2$. In some of these embodiments, the microneedle array area is at least about 0.5 $cm^2$ and up to about 5 $cm^2$. In one embodiment (not shown), a portion of the substrate 14 of the patch 20 is not provided with microneedles (that is, it is non-structured). In some of these embodiments, the non-structured surface has an area of more than about 1 percent and less than about 75 percent of the total area of the device surface that faces a skin surface of a patient. In another of these embodiments, the non-structured surface has an area of more than about 0.10 square inch (0.65 $cm^2$) to less than about 1 square inch (6.5 $cm^2$). In another embodiment (shown in FIG. 2), the microneedles are disposed over substantially the entire surface area of the array 22, such that there is essentially no non-structured area.

In the method of making a medical device described herein, contacting the microneedles with the aqueous composition can be carried out by dip coating the microneedles. Such methods are described, for example, U.S. Pat. App. Publ. No. 2008/0051699 (Choi et al.), the disclosure of which is incorporated herein by reference particularly with reference to FIGS. 10A, 10B, and 10C therein.

Figure 3:
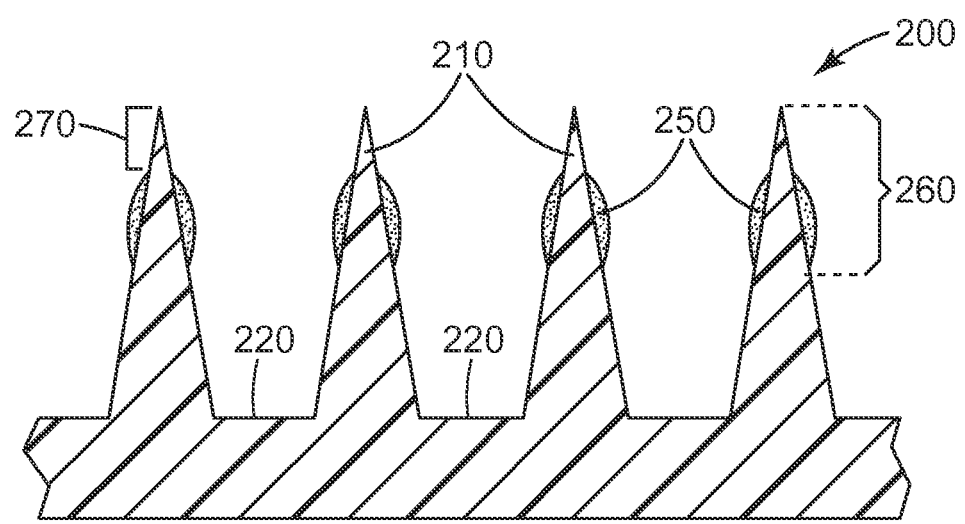
FIG. 3 is a schematic cross-sectional view of a coated microneedle array.

When dip coating, wasting peptide therapeutic agent and amino acid is avoided by contacting only a portion of the microneedle height with the aqueous composition and avoiding contact with the microneedle substrate. FIG. 3 illustrates, in cross-section, a portion of a microneedle array 200 that includes four microneedles 210 (of which two are referenced in FIG. 3) positioned on a microneedle substrate 220. Coating 250 is disposed on microneedles 210 at a distance 260 from the tip of the microneedles. This is accomplished by contacting not more than a portion of the microneedle height with the aqueous composition. Accordingly, in some embodiments, including any one of the method embodiments described herein that includes contacting the microneedles with the aqueous composition, the microneedles each have a tip and a base, the tip extending a distance (h) from the base, and contacting is carried out by contacting the tips of the microneedles and a portion of the microneedles extending not more than 90 percent of the distance (0.9 h) from the tips to the bases with the composition, in some embodiments not more than 70 percent of the distance (0.7 h), or not more than 50 percent of the distance (0.5 h). It is to be understood that the distance can apply to a single microneedle or to an average of the microneedles in an array. In some embodiments, including any one of the embodiments described herein which includes a coating disposed on the microneedles, at least 50% of the microneedles have the coating present on the microneedles near the tip and extending not more than 90 percent of the distance toward the base, preferably not more than 70 percent of the distance, more preferably not more than 50 percent of the distance.

In some embodiments, when the microneedles are contacted with the aqueous composition, the microneedles are facing downward into the aqueous composition. In some of these embodiments, after the microneedles are contacted with the aqueous composition, contacting is terminated and the microneedles are positioned facing upward before and/or during volatilizing a portion of the aqueous composition. In this position, a portion of the aqueous composition remaining on the microneedles may flow toward the base, leaving the tips of the microneedles exposed or with only as small amount of coating on the tips. The degree to which flow occurs can depend upon factors such as the viscosity, contact angle, and surface tension as described above.

After removing the microneedles from the aqueous composition, some of the coating formulation remains on the microneedles, the amount depending upon the aqueous composition properties and surface properties of the microneedle material as described above. At least a portion of the water is removed from the aqueous composition adhering to the microneedles, leaving the coating disposed on the microneedles. One or more additional contacting steps may be used. The shape of the coating, average coating thickness, and amount of the surface of the microneedle covered by the coating depends upon the factors discussed above as well as the number of times the contacting step is repeated.

FIG. 3 illustrates one embodiment with the coating disposed on the microneedles, wherein the tips of the microneedles are essentially exposed (no coating or a relatively small amount of coating) a distance 270 from the tip. In some embodiments, including any one of the embodiments described herein which includes a coating disposed on the microneedles, the tips of the microneedles are exposed or only as small amount of coating is on the tips. In some of these embodiments distance 270 is at least 1 percent (0.1 h), 3 percent (0.03 h) or 6 percent (0.06 h) of the distance from the tip to the base. In some of these embodiments, distance 270 is at most 10 percent (0.1 h) of the distance from the tip to the base.

In some embodiments, including any one of the embodiments described herein which includes a coating disposed on or within the microneedles, the coating is present on the microneedles in an average amount of 0.01 to 2 micrograms per microneedle. Coating weight can be determined by weighing the microneedle array before and after the coating is disposed on the microneedles and dividing the difference by the number of microneedles in the array. This measurement can be made once the coated microneedle array has come to a constant weight, indicating that the water and any other volatilizable carrier has been sufficiently removed, before taking the weight after coating. Alternatively, the total amount of a solid component in the coating on all the microneedles of the entire array can be determined analytically and then the total weight of solids calculated based upon the know weight of all solid components used in the aqueous composition.

Volatilizing the water and any other carrier can be performed using various means including for example, drying at ambient conditions; drying at conditions other than ambient conditions (such as temperatures other than room temperature or a humidity other than an average humidity); drying for various times; drying with heat, lyophilization, freeze drying; other similar techniques; or combinations thereof.

Once a portion of the aqueous composition (which may be a portion or all of the water or non-aqueous solvent) in the aqueous composition has evaporated (either after a single contacting step or multiple contacting steps), the aqueous composition on the microneedle array can be referred to as the "coating" as described above. A coating as described herein can generally be referred to as a dried coating or a solid coating.

In some embodiments, a medical device according to the present disclosure can include an array of dissolvable microneedles. The dissolvable microneedles may contain the peptide therapeutic agent and the amino acid in the various amounts described above for coatings disposed on the microneedles. Dissolvable microneedles further include a dissolvable matrix material. The dissolvable matrix material may be any solid material which dissolves sufficiently in the tissue underlying the stratum corneum to allow the peptide therapeutic agent and amino acid to be released into the tissue. In some embodiments, the dissolvable matrix material is selected from the group consisting of hyaluronic acid, carboxymethylcellulose, hydroxypropylmethylcellulose, methylcellulose, polyvinyl alcohol, polyvinyl pyrrolidone, sucrose, glucose, dextran, trehalose, maltodextrin, and a combination thereof.

Dissolvable microneedle arrays may be fabricated by casting and drying a solution containing volatilizable carrier and dissolvable matrix material (preferably water soluble) in a mold containing the microstructured cavities. The internal shape of the microstructured cavities corresponds to the external shape of the dissolvable microneedles. The mold can be comprised of materials such as polydimethylsiloxane (PDMS) or other plastics that do not permanently bind to or that have low adhesion to materials used to make the dissolvable microneedles.

The peptide therapeutic agent and amino acid component can be incorporated into dissolvable microneedles by first loading a solution of these components with a volatilizable carrier (preferably also including the dissolvable matrix material) into the mold containing microstructured cavities. After at least partially drying (volatilizing at least a portion of the volatilizable carrier), the mold is filled with a solution of dissolvable matrix material (without the peptide therapeutic agent and amino acid), followed by drying. Alternatively, in a one-step process, the peptide therapeutic agent and the amino acid can be combined with the dissolvable matrix material in a solution with the volatilizable carrier and the mold filled with this solution, followed by drying. The volatilizable carriers can include water or any of the volatile non-aqueous solvents (e.g., ethanol) described above. Drying can be carried out using any of the techniques described above.

In embodiments including dissolvable microneedles, the coating comprising the peptide therapeutic agent and the amino acid may be considered to be within a least a portion of the microneedles.

Application of the microneedle device may be carried out by contacting the tissue of a subject with the microneedles and applying hand pressure to force the microneedles into the tissue. Alternatively, an application device may be used which applies the pressure, forcing the microneedles into the tissue. This can provide a more even distribution of pressure and force the microneedles into the tissue at an optimum velocity so that essentially all of the microneedles can release the peptide therapeutic agent into the tissue. In some embodiments, contacting the tissue with a microneedle device is carried out at a microneedle velocity of 5 to 10 meters/second. The "subject" can include humans, sheep, horses, cattle, pigs, dogs, cats, rats, mice, or other mammals.

Some Embodiments of the Disclosure

1. A medical device comprising:
   an array of microneedles; and
   a coating on or within at least a portion of the microneedles, wherein the coating comprises:
   a peptide therapeutic agent; and
   an amino acid,
   wherein the peptide therapeutic agent and the amino acid either both have a net positive charge or both have a net negative charge, and wherein the coating is substantially free of sorbitol.

2. The medical device of embodiment 1, wherein the molar ratio of the amino acid to the peptide therapeutic agent is less than 2:1.

3. The medical device of embodiment 1, wherein the molar ratio of the amino acid to the peptide therapeutic agent is in a range from 0.5:1 to 55:1.

4. The medical device of any one of embodiments 1 to 3, wherein the amino acid is histidine, arginine, lysine, aspartic acid, or glutamic acid.

5. The medical device of embodiment 4, wherein the amino acid is histidine.

6. The medical device of any one of embodiments 1 to 5, wherein the peptide therapeutic agent and the amino acid each have a net positive charge.

7. The medical device of any one of embodiments 1 to 4, wherein the peptide therapeutic agent and the amino acid each have a net negative charge.

8. The medical device of any one of embodiments 1 to 7, wherein the amino acid is present in the coating in a range from 0.1 to 15 percent by weight, based on the total weight of the coating.

9. The medical device of any one of embodiments 1 to 8, wherein the array of microneedles comprises a dissolvable matrix material.

10. The medical device of any one of embodiments 1 to 8, wherein at least some of the microneedles are hollow.

11. A medical device comprising:
an array of microneedles; and
a coating on or within at least a portion of the microneedles, wherein the coating comprises:
a peptide therapeutic agent; and
histidine,
wherein the molar ratio of the histidine to the peptide therapeutic agent is less than 2:1.

12. The medical device of embodiment 11, wherein the molar ratio of the histidine to the peptide therapeutic agent is less than 1.5:1.

13. The medical device of embodiment 11 or 12, wherein the peptide therapeutic agent has a net positive charge.

14. The medical device of embodiment 11 or 12, wherein the peptide therapeutic agent has a net negative charge.

15. The medical device of any one of embodiments 11 to 14, wherein histidine is present in the coating in a range from 0.1 to 15 percent by weight, based on the total weight of the coating.

16. The medical device of any one of embodiments 11 to 15, wherein the histidine stabilizes the peptide therapeutic agent in the coating.

17. The medical device of any preceding embodiment, wherein the peptide therapeutic agent is parathryoid hormone, calcitonin, lysozyme, insulin, glatiramer acetate, goserelin acetate, octreotide, leuprolide, vasopressin, atrial natriuretic peptide (ANP), vascular endothelial growth factor (VEGF), fibroblast growth factor (FGF), erythropoietin (EPO), bone morphogenetic proteins (BMPs), epidermal growth factor (EFG), granulocyte clony-stimulating factor (G-CSF), granulocyte macrophage colony stimulating factor (GM-CSF), interferon alpha, interferon beta, interferon gamma, antimicrobial peptides, dornase alfa, tissue plasminogen activator, a fusion protein, or a vaccine.

18. The medical device of any preceding embodiment, wherein the coating is present on the microneedles in an average amount of 0.01 to 2 micrograms per microneedle.

19. A method of making a medical device comprising microneedles, the method comprising:
providing an aqueous composition comprising a peptide therapeutic agent, an amino acid, and a buffer, wherein the peptide therapeutic agent and the amino acid either both have a net positive charge or both have a net negative charge in the aqueous composition;
contacting the microneedles with the aqueous composition; and
volatilizing a portion of the aqueous composition to provide a coating on at least a portion of the microneedles, wherein the coating comprises at least the peptide therapeutic agent and the amino acid.

20. The method of embodiment 19, wherein the buffer comprises phosphate, acetate, citrate, or tris(hydroxymethyl)aminomethane.

21. A method of stabilizing a peptide therapeutic agent in a coating on an array of microneedles, the method comprising incorporating an amino acid into the coating, wherein the peptide therapeutic agent and the amino acid either both have a net positive charge or both have a net negative charge.

22. The method of any one of embodiments 19 to 21, wherein the molar ratio of the amino acid to the peptide therapeutic agent is less than 2:1.

23. The method of any one of embodiments 19 to 21, wherein the molar ratio of the amino acid to the peptide therapeutic agent is in a range from 0.5:1 to 55:1.

24. The method of any one of embodiments 19 to 23, wherein the amino acid is histidine, arginine, lysine, aspartic acid, or glutamic acid.

25. The method of embodiment 24, wherein the amino acid is histidine.

26. The method of any one of embodiments 19 to 25, wherein the peptide therapeutic agent and the amino acid each have a net positive charge.

27. The method of any one of embodiments 19 to 25, wherein the peptide therapeutic agent and the amino acid each have a net negative charge.

28. The method of any one of embodiments 19 to 27, wherein the amino acid is present in the coating in a range from 0.1 to 15 percent by weight, based on the total weight of the coating.

29. The method of any one of embodiments 19 to 28, wherein the aqueous composition has a pH in a range from 3 to 11.

30. The method of any one of embodiments 19 to 39, wherein the aqueous composition or the coating is substantially free of sorbitol.

31. A method of making a medical device comprising microneedles, the method comprising:
providing an aqueous composition comprising a peptide therapeutic agent, histidine, and a buffer, wherein the molar ratio of the histidine to the peptide therapeutic agent in the aqueous composition is less than 2:1;
contacting the microneedles with the aqueous composition; and
volatilizing a portion of the aqueous composition to provide a coating on at least a portion of the microneedles, wherein the coating comprises at least the peptide therapeutic agent and the histidine.

32. The method of embodiment 31, wherein the aqueous composition has a pH in a range from 3 to 11.

33. The method of embodiment 31 or 32, wherein the molar ratio of histidine to the peptide therapeutic agent is less than 1.5:1.

34. The method of embodiment 31, 32, or 33, wherein the peptide therapeutic agent has a net positive charge.

35. The method of embodiment 31, 32, or 33, wherein the peptide therapeutic agent has a net negative charge.

36. The method of any one of embodiments 31 to 35, wherein histidine is present in the coating in a range from 0.1 to 15 percent by weight, based on the total weight of the coating.

37. The method of any one of embodiments 31 to 36, wherein buffer comprises phosphate, acetate, citrate, or tris(hydroxymethyl)aminomethane.

38. The method of any one of embodiments 19 to 37, wherein the wherein the peptide therapeutic agent is parathryroid hormone, calcitonin, lysozyme, insulin, glatiramer acetate, goserelin acetate, octreotide, leuprolide, vasopressin, atrial natriuretic peptide (ANP), vascular endothelial growth factor (VEGF), fibroblast growth factor (FGF), erythropoietin (EPO), bone morphogenetic proteins (BMPs), epidermal growth factor (EFG), granulocyte clony-stimulating factor (G-CSF), granulocyte macrophage colony stimulating factor (GM-CSF), interferon alpha, interferon beta, interferon gamma, antimicrobial peptides, dornase alfa, tissue plasminogen activator, a fusion protein, or a vaccine.

39. The method of any one of embodiments 19 to 38, wherein the coating is present on the microneedles in an average amount of 0.01 to 2 micrograms per microneedle.

40. A method of making a medical device comprising microneedles according to any one of embodiments 1 to 10, the method comprising:
providing an aqueous composition comprising the peptide therapeutic agent and the amino acid;
contacting the microneedles with the aqueous composition; and
volatilizing a portion of the aqueous composition to provide a coating on at least a portion of the microneedles, wherein the coating comprises at least the peptide therapeutic agent and the amino acid.

41. A method of making a medical device comprising microneedles according to any one of embodiments 11 to 16, the method comprising:
providing an aqueous composition comprising the peptide therapeutic agent and the histidine;
contacting the microneedles with the aqueous composition; and
volatilizing a portion of the aqueous composition to provide a coating on at least a portion of the microneedles, wherein the coating comprises at least the peptide therapeutic agent and the histidine.

The following examples are provided to more particularly illustrate various embodiments of the present invention, but the particular materials and amounts thereof recited in these examples, as well as other conditions and details are in no way intended to limit this invention.

EXAMPLES

Materials

The microneedle arrays were injection molded using VECTRA MT 1300 thermoplastic liquid crystal polymer (LCP) (Ticona Engineering Polymers, Florence, Ky.). The microneedle arrays featured four-sided pyramidal shaped microneedles having heights of about 500 microns and an aspect ratio of approximately 3:1. The microneedles were arranged in an octagon shaped pattern of about 316 microneedles with equal spacing between individual microneedles of about 550 microns (as measured from tip to tip).

PTH, parathyroid hormone (1-34) (human), was obtained as the acetate salt from Bachem, Torrence, Calif. Salmon calcitonin and lysozme were obtained from Calbiochem, LaJolla, Calif. Insulin was obtained from Sigma-Aldrich, St. Louis, Mo.

L-Histidine monohydrochloride (His-HCl) was obtained from J. T. Baker, Phillipsburg, N.J.

L-Arginine hydrochloride (Arg-HCl) was obtained from Spectrum Chemical, New Brunswick, N.J.

Phosphate buffered saline (1×PBS) was obtained from Amresco LLC, Solon, Ohio.

The protein or polypeptide content in the formulation coated on the microneedle arrays was determined using an Agilent 1100 HPLC system (Agilent Technologies, Wilmington, Del.) equipped with a binary pump, well-plated thermostated autosampler, thermostated column compartment, and a diode array UV detector. A Zorbax 300SB-C8 column (Agilent Technologies, Wilmington, Del.) having a 5 µm particle size and 2.1×150 mm inner diameter was used for the separations. The column was maintained at 50° C. The mobile phase consisted of two eluents. Eluent A was 0.1% TFA (trifluoroacetic acid) in water and eluent B was 0.1% TFA in acetonitrile (Spectrum Chemical, New Brunswick, N.J.). A linear gradient from 80/20 to 50/50 (A/B) was applied over 30 minutes. The flow rate was 0.4 mL/minute and the UV detection wavelength was set at 214 nm. The total run time was 34 minutes and the sample injection volume was 15 µL.

The pH of the formulations was determined using pH color indicating strips (available from EMD Chemicals, Gibbstown, N.J. under the trade designation "COLOR-pHAST").

Example 1

A sample formulation containing 10 mg/mL of PTH and 12 mg/mL of L-histidine monohydrochloride (His-HCl) in phosphate buffered saline (PBS) was prepared. The pH of the sample formulation was 5.5-6.0. A control formulation was also prepared containing 10 mg/mL of PTH in PBS. The control formulation did not have His-HCl in the formulation. The pH of the control formulation was 6.0. Microneedle arrays were coated with either the sample or the control formulation. The coating was applied by dropwise addition of 50 µL of the formulation to the portion of the array defined by the octagon shaped pattern of microneedles. The flood coated arrays (both sample and control formulation coated) were dried in an oven at 35° C. for about 15 hours.

After drying, the coated arrays were placed in a storage chamber that was maintained at 40° C. and 96% relative humidity (RH). The PTH content of the coated arrays was determined following storage in the chamber for 1, 3, 7, and 14 days. At the designated time point, an array was taken from the chamber and washed with PBS (2 mL) to remove the coating from the array. An aliquot of the resulting wash solution was analyzed for PTH content using the HPLC method described above. Reference standards were prepared by measuring the initial PTH content of freshly coated arrays (both sample and control formulation coated). The arrays used as reference standards were stored in a refrigerator at about 4° C. and analyzed within one day of being prepared. At each time point, the percentage of undegraded PTH remaining in the sample or control coatings was determined by measuring the peak area for PTH in the selected coating and dividing it by the peak area measured for PTH in the corresponding reference standard. The results are reported in Table 1.

TABLE 1

| | Percent of Initial PTH Content in the Coating | | | | |
|---|---|---|---|---|---|
| Amino Acid | Initial | Day 1 | Day 3 | Day 7 | Day 14 |
| None (control) | 100 | 1.3 | 0 | 0 | 0 |
| L-Histidine | 100 | 85.2 | 60.3 | 23.1 | 11.0 |

Example 2

The same procedure as described in Example 1 was used with the exception that the sample formulation contained 12 mg/mL of L-arginine hydrochloride, instead of L-histidine monohydrochloride. The pH of the sample formulation was 6.0. The results are reported in Table 2.

TABLE 2

| | Percent of Initial PTH Content in the Coating | | | | |
|---|---|---|---|---|---|
| Amino Acid | Initial | Day 1 | Day 3 | Day 7 | Day 14 |
| None (control) | 100 | 1.3 | 0 | 0 | 0 |
| L-Arginine | 100 | 3.5 | 0.8 | 0.4 | 0 |

Example 3

A sample formulation containing 5 mg/mL of salmon calcitonin and 12 mg/mL of L-histidine monohydrochloride (His-HCl) in PBS was prepared. The pH of the sample formulation was 5.5. A control formulation was also prepared containing 5 mg/mL of salmon calcitonin in PBS. The control formulation did not have His-HCl in the formulation. The pH of the control formulation was 6.0-6.5. Microneedle arrays were coated with either the sample or the control formulation. The coating was applied by dropwise addition of 50 µL of the formulation to the portion of the array defined by the octagon shaped pattern of microneedles. The flood coated arrays (both sample and control formulation coated) were dried in an oven at 35° C. for about 15 hours.

After drying, the coated arrays were placed in a storage chamber that was maintained at 40° C. and 96% relative humidity (RH). The salmon calcitonin content of the coated arrays was determined following storage in the chamber for 1, 3, 7, and 14 days. At the designated time point, an array was taken from the chamber and washed with PBS (1 mL) to remove the coating from the array. An aliquot of the resulting wash solution was analyzed for salmon calcitonin content using the HPLC method described above. Reference standards were prepared by measuring the initial salmon calcitonin content of freshly coated arrays (both sample and control formulation coated). The arrays used as reference standards were stored in a refrigerator at about 4° C. and analyzed within one day of being prepared. The percentage of undegraded salmon calcitonin remaining in the coating at each time point was determined by measuring the peak area for salmon calcitonin in the selected coating and dividing it by the peak area measured for salmon calcitonin in the corresponding reference standard. The results are reported in Table 3.

TABLE 3

| | Percent of Initial Salmon Calcitonin Content in the Coating | | | | |
|---|---|---|---|---|---|
| Amino Acid | Initial | Day 1 | Day 3 | Day 7 | Day 14 |
| None (control) | 100 | 21.5 | 0.9 | 0.1 | 0 |
| L-Histidine | 100 | 30.3 | 31.7 | 7.5 | 2.7 |

Example 4

The same procedure as described in Example 3 was used with the exception that the sample formulation contained 12 mg/mL of L-arginine hydrochloride, instead of L-histidine monohydrochloride. The pH of the sample formulation was 6.0-6.5. The results are reported in Table 4.

TABLE 4

| | Percent of Initial Salmon Calcitonin Content in the Coating | | | | |
|---|---|---|---|---|---|
| Amino Acid | Initial | Day 1 | Day 3 | Day 7 | Day 14 |
| None (control) | 100 | 21.5 | 0.9 | 0.1 | 0 |
| L-Arginine | 100 | 5.8 | 0.3 | 0 | 0 |

Example 5

A sample formulation containing 5 mg/mL of insulin and 12 mg/mL of L-histidine monohydrochloride (His-HCl) in 0.1 N acetic acid was prepared. The pH of the sample formulation was 3.0-3.5. A control formulation was also prepared containing 5 mg/mL of insulin in 0.1 N acetic acid. The control formulation did not have His-HCl in the formulation. The pH of the control formulation was 3.0-3.5. Microneedle arrays were coated with either the sample or the control formulation. The coating was applied by dropwise addition of 50 µL of the formulation to the portion of the array defined by the octagon shaped pattern of microneedles. The flood coated arrays (both sample and control formulation coated) were dried in an oven at 35° C. for about 15 hours.

After drying, the coated arrays were placed in a storage chamber that was maintained at 40° C. and 96% relative humidity (RH). The insulin content of the coated arrays was determined following storage in the chamber for 1, 3, 7, and 14 days. At the designated time point, an array was taken from the chamber and washed with 0.1 N acetic acid (1 mL) to remove the coating from the array. The resulting wash solution was analyzed for insulin content using the HPLC method described above. Reference standards were prepared by measuring the insulin content of freshly coated arrays (both sample and control formulation coated). The arrays used as reference standards were stored in a refrigerator at about 4° C. and analyzed within one day of being prepared. The percentage of undegraded insulin remaining in the coating at each time point was determined by measuring the peak area for insulin in the selected coating and dividing it by the peak area measured for insulin in the corresponding reference standard. The results are reported in Table 5.

TABLE 5

| | Percent of Initial Insulin Content in the Coating | | | | |
|---|---|---|---|---|---|
| Amino Acid | Initial | Day 1 | Day 3 | Day 7 | Day 14 |
| None (control) | 100 | 7.8 | 0 | 0 | 0 |
| L-Histidine | 100 | 95.3 | 93.5 | 79.2 | 34.9 |

Example 6

The same procedure as described in Example 5 was used with the exception that the sample formulation contained 12 mg/mL of L-arginine hydrochloride, instead of L-histidine monohydrochloride. The pH of the sample formulation was 3.0-3.5. The results are reported in Table 6.

TABLE 6

| | Percent of Initial Insulin Content in the Coating | | | | |
|---|---|---|---|---|---|
| Amino Acid | Initial | Day 1 | Day 3 | Day 7 | Day 14 |
| None (control) | 100 | 7.8 | 0 | 0 | 0 |
| L-Arginine | 100 | 75.4 | 45.9 | 27.1 | 6.1 |

Example 7

A sample formulation containing 10 mg/mL of lysozyme and 12 mg/mL of L-histidine monohydrochloride (His-HCl) in PBS was prepared. The pH of the sample formulation was 5.5-6.0. A control formulation was also prepared containing 10 mg/mL of lysozyme in PBS. The control formulation did not have His-HCl in the formulation. The pH of the control formulation was 6.5. Microneedle arrays were coated with either the sample or the control formulation. The coating was applied by dropwise addition of 50 μL of the formulation to the portion of the array defined by the octagon shaped pattern of microneedles. The flood coated arrays (both sample and control formulation coated) were dried in an oven at 35° C. for about 15 hours.

After drying, the coated arrays were placed in a storage chamber that was maintained at 40° C. and 96% relative humidity (RH). The lysozyme content of the coated arrays was determined following storage in the chamber for 1, 3, 7, and 14 days. At the designated time point, an array was taken from the chamber and washed with PBS (2 mL) to remove the coating from the array. An aliquot of the resulting wash solution was analyzed for lysozyme content using the HPLC method described above. Reference standards were prepared by measuring the lysozyme content of freshly coated arrays (both sample and control formulation coated). The arrays used as reference standards were stored in a refrigerator at about 4° C. and analyzed within one day of being prepared. The percentage of undegraded lysozyme remaining in the coating at each time point was determined by measuring the peak area for lysozyme in the selected coating and dividing it by the peak area measured for lysozyme in the corresponding reference standard. The results are reported in Table 7.

TABLE 7

| Amino Acid | Percent of Initial Lysozyme Content in the Coating | | | | |
|---|---|---|---|---|---|
| | Initial | Day 1 | Day 3 | Day 7 | Day 14 |
| None (control) | 100 | 26.9 | 4.4 | 1.9 | 1.9 |
| L-Histidine | 100 | 100.0 | 80.6 | 60.1 | 53.3 |

Example 8

The same procedure as described in Example 7 was used with the exception that the sample formulation contained 12 mg/mL of L-arginine hydrochloride, instead of L-histidine monohydrochloride. The pH of the sample formulation was 6.5. The results are reported in Table 8.

TABLE 8

| Amino Acid | Percent of Initial Lysozyme Content in the Coating | | | | |
|---|---|---|---|---|---|
| | Initial | Day 1 | Day 3 | Day 7 | Day 14 |
| None (control) | 100 | 26.9 | 4.4 | 1.9 | 1.9 |
| L-Arginine | 100 | 52.6 | 33.1 | 22.4 | 23.0 |

This disclosure may take on various modifications and alterations without departing from its spirit and scope. Accordingly, this disclosure is not limited to the above-described embodiments but is to be controlled by the limitations set forth in the following claims and any equivalents thereof.

What is claimed is:

1. A medical device comprising:
   an array of microneedles; and
   a coating on or within at least a portion of the microneedles, wherein the coating comprises:
      a peptide therapeutic agent; and
      an amino acid,
   wherein the coating is substantially free of sorbitol, and wherein one of the following is true:
      the peptide therapeutic agent has a net positive charge at a pH in a range from 7 to 7.4, and the amino acid has a net positive charge at the pH; or
      the peptide therapeutic agent has a net negative charge at a pH in a range from 7 to 7.4, and the amino acid has a net negative charge at the pH.

2. The medical device of claim 1, wherein the amino acid is histidine, arginine, lysine, aspartic acid, or glutamic acid.

3. The medical device of claim 2, wherein the amino acid is histidine.

4. The medical device of claim 1, wherein the peptide therapeutic agent has a net positive charge at the pH, and the amino acid has a net positive charge at the pH.

5. A medical device comprising:
   an array of microneedles; and
   a coating on or within at least a portion of the microneedles, wherein the coating comprises:
      a peptide therapeutic agent; and
      histidine,
   wherein the molar ratio of the histidine to the peptide therapeutic agent is less than 2.1.

6. The medical device of claim 5, wherein the molar ratio of the histidine to the peptide therapeutic agent is less than 1.5:1.

7. The medical device of claim 5, wherein the peptide therapeutic agent has a net positive charge.

8. The medical device of claim 5, wherein the histidine stabilizes the peptide therapeutic agent in the coating.

9. The medical device of claim 1, wherein the array of microneedles comprises a dissolvable matrix material or wherein at least a portion of the microneedles are hollow.

10. A method of making the medical device of claim 1, the method comprising:
    providing an aqueous composition comprising a peptide therapeutic agent, an amino acid, and a buffer, wherein the aqueous composition has a pH, wherein the peptide therapeutic agent has a net positive charge at the pH of the aqueous composition, and the amino acid has a net positive charge at the pH of the aqueous composition, or wherein the peptide therapeutic agent has a net negative charge at the pH of the aqueous composition, and the amino acid has a net negative charge at the pH of the aqueous composition;
    contacting the microneedles with the aqueous composition; and
    volatilizing a portion of the aqueous composition to provide a coating on at least a portion of the microneedles, wherein the coating comprises at least the peptide therapeutic agent and the amino acid.

11. The method of claim 10, wherein the pH of the aqueous composition is in a range from 3 to 11.

12. The method of claim 10, wherein the amino acid stabilizes the peptide therapeutic agent on or within an array of the microneedles.

13. The method of claim 10, wherein the amino acid is histidine, arginine, lysine, aspartic acid, or glutamic acid.

14. The method of claim 10, wherein the peptide therapeutic agent has a net positive charge at the pH of the aqueous composition, and the amino acid has a net positive charge at the pH of the aqueous composition.

15. A method of making the medical device of claim 5, the method comprising:
    providing an aqueous composition comprising the peptide therapeutic agent, histidine, and a buffer, wherein the molar ratio of the histidine to the peptide therapeutic agent in the aqueous composition is less than 2:1;
    contacting the microneedles with the aqueous composition; and
    volatilizing a portion of the aqueous composition to provide a coating on at least a portion of the microneedles, wherein the coating comprises at least the peptide therapeutic agent and the histidine.

16. The method of claim 10, wherein the buffer comprises phosphate, acetate, citrate, or tris(hydroxymethyl)aminomethane.

17. The medical device of claim 5, wherein the peptide therapeutic agent is parathryroid hormone, calcitonin, lysozyme, insulin, glatiramer acetate, goserelin acetate, octreotide, leuprolide, vasopressin, atrial natriuretic peptide (ANP), vascular endothelial growth factor (VEGF), fibroblast growth factor (FGF), erythropoietin (EPO), bone morphogenetic proteins (BMPs), epidermal growth factor (EFG), granulocyte clony-stimulating factor (G-CSF), granulocyte macrophage colony stimulating factor (GM-CSF), interferon alpha, interferon beta, interferon gamma, antimicrobial peptides, dornase alfa, tissue plasminogen activator, a fusion protein, or a vaccine.

18. The medical device of claim 1, wherein the molar ratio of the amino acid to the peptide therapeutic agent is less than 2:1.

19. The medical device of claim 1, wherein the molar ratio of the amino acid to the peptide therapeutic agent is in a range from 0.5:1 to 55:1.

20. The medical device of claim 1, wherein the peptide therapeutic agent is parathryroid hormone, calcitonin, lysozyme, insulin, glatiramer acetate, goserelin acetate, octreotide, leuprolide, vasopressin, atrial natriuretic peptide (ANP), vascular endothelial growth factor (VEGF), fibroblast growth factor (FGF), erythropoietin (EPO), bone morphogenetic proteins (BMPs), epidermal growth factor (EFG), granulocyte clony-stimulating factor (G-CSF), granulocyte macrophage colony stimulating factor (GM-CSF), interferon alpha, interferon beta, interferon gamma, antimicrobial peptides, dornase alfa, tissue plasminogen activator, a fusion protein, or a vaccine.

* * * * *